United States Patent
Hwang et al.

(10) Patent No.: US 11,491,102 B2
(45) Date of Patent: Nov. 8, 2022

(54) COMPOSITION FOR SKIN ANTI-INFLAMMATION AND SKIN MOISTURIZING COMPRISING ARTEMISIA EXTRACT EXTRACTED WITH SKIN COSMETIC SOLUTION AS A SOLVENT

(71) Applicant: Amorepacific Corporation, Seoul (KR)

(72) Inventors: Joonyoung Hwang, Yongin-si (KR); Byungryol Paik, Yongin-si (KR); Jinsup Shim, Yongin-si (KR); Eun Soo Lee, Yongin-si (KR)

(73) Assignee: Amorepacific Cornoration, Seoul (KR)

( * ) Notice: Subject to any disclaimer, the term of this patent is extended or adjusted under 35 U.S.C. 154(b) by 0 days.

(21) Appl. No.: 16/887,300

(22) Filed: May 29, 2020

(65) Prior Publication Data

US 2020/0375884 A1 Dec. 3, 2020

(30) Foreign Application Priority Data

May 30, 2019 (KR) .................. 10-2019-0063802

(51) Int. Cl.
| | | |
|---|---|---|
| *A61K 8/9789* | (2017.01) | |
| *A61K 8/41* | (2006.01) | |
| *A61K 8/06* | (2006.01) | |
| *A61Q 19/00* | (2006.01) | |
| *A61K 8/60* | (2006.01) | |

(52) U.S. Cl.
CPC .......... *A61K 8/9789* (2017.08); *A61K 8/062* (2013.01); *A61K 8/416* (2013.01); *A61K 8/60* (2013.01); *A61Q 19/007* (2013.01)

(58) Field of Classification Search
CPC .... A61K 9/00; A61K 2236/00; A61K 8/9794; A61K 36/00; A61K 8/60; A61Q 19/00; A61Q 19/007
See application file for complete search history.

(56) References Cited

U.S. PATENT DOCUMENTS

| 2013/0149322 A1* | 6/2013 | van Spronsen | C07H 17/07 549/400 |
| 2013/0156873 A1* | 6/2013 | Florence | A61K 8/9789 424/757 |
| 2014/0335207 A1* | 11/2014 | Minton | A61K 33/00 424/718 |

FOREIGN PATENT DOCUMENTS

| CN | 1304020 C | * | 3/2007 | ............ A61K 35/78 |
| JP | 04342519 A | * | 11/1992 | |
| KR | 10-2010-0059719 A | | 6/2010 | |
| KR | WO2012067404 A2 | * | 5/2012 | ........... A61K 36/282 |
| KR | 10-2016-0045271 A | | 4/2016 | |

OTHER PUBLICATIONS

Bergfeld et al, Safety Assesment of Alkyl Betaines , May 13, 2013 (Year: 2013).*
Machine Translation of CN1304020C (pp. 1-6) (Year: 2007).*
Machine Translation of WO2012067404A2 (pp. 1-11) (Year: 2012).*
SoonSkinCare blog (https://soonskincare.com/blogs/news/ingredient-spotlight-betaine) published Mar. 12, 2019. pp. 1-3 (Year: 2019).*
Machine translation of JP-04342519-A. pp. 1-11. Published Nov. 30, 1992 (Year: 1992).*
Jang, M. et al. "Extraction Optimization for Obtaining Artemisia capillaris Extract with High Anti-Inflammatory Activity in RAW 264.7 Macrophage Cells" Biomed Research International 2015, ID 872718, pp. 1-9 (Year: 2015).*

* cited by examiner

*Primary Examiner* — Andrew S Rosenthal
(74) *Attorney, Agent, or Firm* — Sughrue Mion, PLLC

(57) ABSTRACT

The present disclosure discloses a composition for skin anti-inflammation and skin moisturizing, which contains an *Artemisia* extract extracted using a skin cosmetic solution as an extraction solvent as an active ingredient. Specifically, the composition according to the present disclosure, which contains the *Artemisia* extract obtained using an effective and safe extraction solvent, may exhibit superior skin safety and usability as well as superior anti-inflammatory and moisturizing effects. In addition, the composition according to the present disclosure, which contains the *Artemisia* extract extracted using the skin cosmetic solution that can be used as a cosmetic ingredient as an extraction solvent, may superbly maintain *Artemisia* flavor without an additional flavoring agent.

5 Claims, 2 Drawing Sheets

COMPOSITION FOR SKIN ANTI-INFLAMMATION AND SKIN MOISTURIZING COMPRISING ARTEMISIA EXTRACT EXTRACTED WITH SKIN COSMETIC SOLUTION AS A SOLVENT

CROSS-REFERENCE TO RELATED APPLICATION

This application claims the priority of Korean Patent Application No. 10-2019-0063802, filed on May 30, 2019 and all the benefits accruing therefrom under 35 U.S.C. § 119, the contents of which in its entirety are herein incorporated by reference.

BACKGROUND

1. Field

The present disclosure relates to a composition for skin anti-inflammation and skin moisturizing, which contains an *Artemisia* extract extracted using a skin cosmetic solution as an extraction solvent as an active ingredient.

2. Description of the Related Art

Extraction is a process of dissolving and separating a specific component in a solid or liquid mixture mainly using a liquid solvent. It is a very important separation method not only in chemical and biological experiments but also in industrial applications. The extraction can be achieved using chemical reactions such as acid-base reaction, chelation, etc. or simply using the difference in solubility. Solid-liquid extraction refers to extraction from solid, and liquid-liquid extraction refers to extraction from liquid. The solid-liquid extraction is often called leaching.

Among the extraction methods, solvent extraction refers to separation of a component (sometimes, two or more components) from a solid or liquid sample by dissolving using a solvent. When a mixture is subjected to chemical analysis or application, a specific component may dissolve well in a particular solvent, whereas other components does not.

An extraction solvent refers to a liquid solvent used to dissolve and separate a specific substance from a solid mixture or a liquid mixture, such as water, alcohols, ethers, petroleum ether, benzene, ethyl acetate, chloroform, etc. Recently, supercritical fluids (SCFs) are frequently used as solvents for extraction.

Although extraction can be performed using solvents only as described above, it can be achieved through chemical reactions such as acid-base reaction or chelation from a mixture. A Soxhlet extractor is used for extraction of a solid mixture using a solvent, and a separatory funnel is used for extraction of a liquid mixture.

The existing cosmetic compositions containing plant extracts are prepared by extracting raw materials using generally used extractions and then reducing the same. In general, after conducting extraction using an organic solvent, water or a mixture thereof as a solvent and removing the solvent through evaporation, the obtained extract is processed into a form suitable for use in a cosmetic composition.

Although the use of the common extraction method is effective in terms of cost or time, it may be problematic in that only the components soluble in the solvent are extracted from among the components of the raw material and some of the components may be lost after the extraction. In addition, a small amount of the organic solvent remaining after the extraction may cause undesired reactions when the cosmetic composition is applied onto skin, which lowers the effect of the extract on the skin and makes it difficult for the function of the cosmetic composition to be exerted. In addition, there may occur a skin-related safety problem.

SUMMARY

The present disclosure is directed to providing a composition exhibiting superior skin safety and usability and superior anti-inflammatory and moisturizing effects by containing an *Artemisia* extract obtained using an effective and safe extraction solvent.

The present disclosure is also directed to providing a composition containing an *Artemisia* extract extracted using a skin cosmetic solution that can be used as a cosmetic ingredient as an extraction solvent, which superbly maintains *Artemisia* flavor without an additional flavoring agent.

An exemplary embodiment of the present disclosure provides a composition for skin moisturizing containing an *Artemisia* extract extracted using a skin cosmetic solution as an extraction solvent as an active ingredient.

In addition, an exemplary embodiment of the present disclosure provides a composition for skin anti-inflammation containing an *Artemisia* extract extracted using a skin cosmetic solution as an extraction solvent as an active ingredient.

The composition according to the present disclosure, which contains the *Artemisia* extract obtained using an effective and safe extraction solvent, may exhibit superior skin safety and usability as well as superior anti-inflammatory and moisturizing effects.

In addition, the composition according to the present disclosure, which contains the *Artemisia* extract obtained using an effective and safe extraction solvent, may superbly maintain *Artemisia* flavor without an additional flavoring agent.

DETAILED DESCRIPTION

Figure 1:
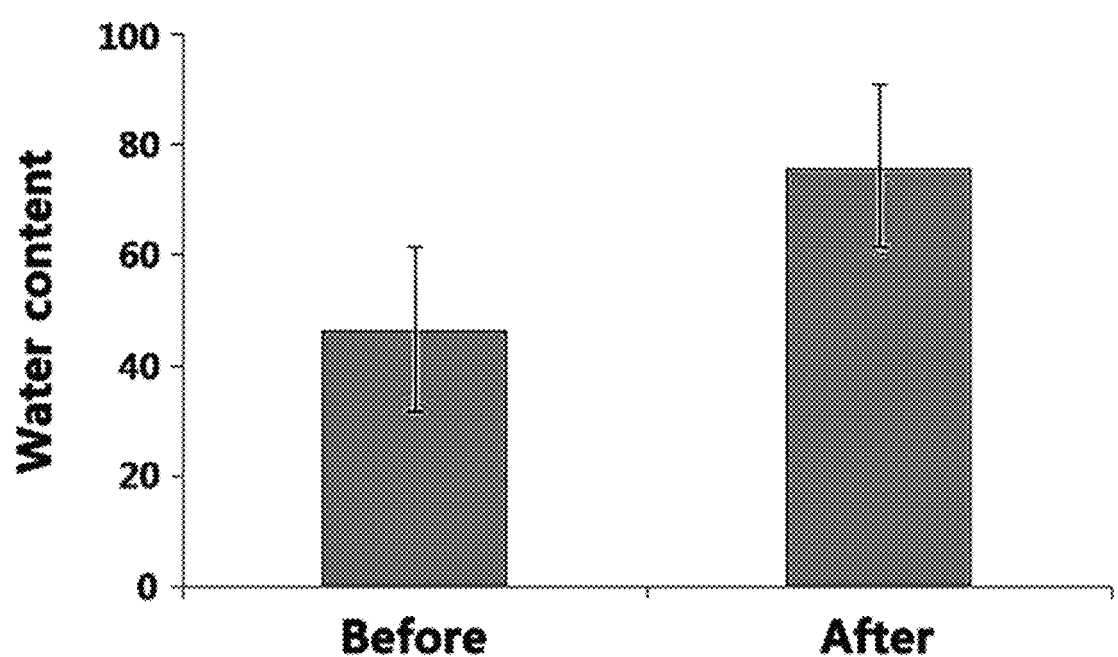
FIG. 1 shows a result of evaluating the skin moisturizing effect of an *Artemisia* extract according to the present disclosure in Test Example 2.

As used herein, a "skin cosmetic solution" collectively refers to a composition with fluidity, which can be applied to skin for various beauty care purposes. It mainly includes a liquid or essence formulation such as a softening lotion, a nourishing lotion, an emulsion, etc. and may contain an emulsifier, a solubilizer, a humectant, water and a drug.

As used herein, an "extract" includes any substance extracted from a natural product, regardless of extraction method, extraction solvent, extracted ingredients or type of extract the extract. It is used in a broad concept, including any substance that can be obtained by otherwise processing or treating the extracted substance. Specifically, the processing or treatment may be fermentation or enzymatic treatment of the extract. Accordingly, in the present specification, the term extract is used in a broad concept, including a fermentation product, a concentrate and a dried product.

As used herein, a "glycerin derivative" refers to a compound similar to glycerin, which is obtained as a portion of glycerin is chemically modified. It refers to a compound in which a hydrogen atom or a specific radical of glycerin is replaced by another atom or radical.

Hereinafter, the present disclosure is described in detail.

In an aspect, the present disclosure may relate to a composition for skin moisturizing or a composition for skin anti-inflammation, which contains an *Artemisia* extract extracted using a skin cosmetic solution as an extraction solvent as an active ingredient.

In another aspect, the present disclosure may relate to a method for skin moisturizing, which comprises administering an *Artemisia* extract extracted using a skin cosmetic solution as an extraction solvent to a subject in need thereof.

In another aspect, the present disclosure may relate to a method for skin anti-inflammation, which comprises administering an *Artemisia* extract extracted using a skin cosmetic solution as an extraction solvent to a subject in need thereof.

In an exemplary embodiment, the *Artemisia* may be *Artemisia argyi, Artemisia princeps, Artemisia montana, Artemisia capillaris, Artemisia annua, Artemisia vulgaris, Artemisia scoparia, Artemisia sieversiana, Artemisia dracunculus, Artemisia absinthium, Artemisia abrotanum* or *Artemisia umbelliformis*, although not being limited thereto. Specifically, it may be *Artemisia argyi, Artemisia princeps, Artemisia montana, Artemisia capillaris, Artemisia annua* or *Artemisia vulgaris*.

In an exemplary embodiment, the skin cosmetic solution may contain one or more selected from a group consisting of a $C_2$-$C_{20}$ dihydric alcohol and a $C_2$-$C_{20}$ trihydric alcohol.

In another exemplary embodiment, the dihydric alcohol may be one or more selected from a group consisting of butylene glycol, propanediol and hexanediol. In addition, the trihydric alcohol may be one or more of glycerin and a glycerin derivative.

In another exemplary embodiment, the butylene glycol may be 1,3-butylene glycol, the propanediol may be 1,3-propanediol, and the hexanediol may be 1,2-hexanediol.

In another exemplary embodiment, the glycerin derivative may be ethylhexylglycerin.

In another exemplary embodiment, the skin cosmetic solution may contain glycerin, butylene glycol, propanediol, hexanediol and ethylhexylglycerin.

In another exemplary embodiment, the skin cosmetic solution may further contain at least one of D-glucose and betaine.

In an exemplary embodiment, the content of the butylene glycol may be 10-25 wt % based on the total weight of the skin cosmetic solution. If the content exceeds 25 wt %, usability may be poor due to increased viscosity, difficulty of filtration, etc. If the content is below 10 wt %, the effect of extraction may decrease remarkably. In an aspect, the content of the butylene glycol may be 10 wt % or higher, 12 wt % or higher, 14 wt % or higher, 16 wt % or higher, 18 wt % or higher, 20 wt % or higher, 22 wt % or higher, or 24 wt % or higher, and 25 wt % or lower, 22 wt % or lower, 20 wt % or lower, 18 wt % or lower, 16 wt % or lower, 14 wt % or lower, or 12 wt % or lower, based on the total weight of the skin cosmetic solution.

In another exemplary embodiment, the content of the propanediol may be 1-20 wt % based on the total weight of the skin cosmetic solution. If the content exceeds 20 wt %, usability may be poor due to increased viscosity, difficulty of filtration, etc. If the content is below 1 wt %, the effect of extraction may decrease remarkably. In an aspect, the content may be 1 wt % or higher, 4 wt % or higher, 6 wt % or higher, 8 wt % or higher, 10 wt % or higher, 12 wt % or higher, 14 wt % or higher, 16 wt % or higher, or 18 wt % or higher. In addition, the content may be 20 wt % or lower, 18 wt % or lower, 16 wt % or lower, 14 wt % or lower, 12 wt % or lower, 10 wt % or lower, 8 wt % or lower, 6 wt % or lower, 4 wt % or lower, or 2 wt % or lower.

In another exemplary embodiment, the content of the hexanediol may be 0.1-5 wt % based on the total weight of the skin cosmetic solution. If the content exceeds 5 wt %, usability may be poor due to increased viscosity, difficulty of filtration, etc. If the content is below 0.1 wt %, the effect of extraction may decrease remarkably. In an aspect, the content may be 0.1 wt % or higher, 0.4 wt % or higher, 0.6 wt % or higher, 0.8 wt % or higher, 1 wt % or higher, 1.2 wt % or higher, 1.5 wt % or higher, 2 wt % or higher, 2.5 wt % or higher, 3 wt % or higher, 3.5 wt % or higher, 4 wt % or higher, or 4.5 wt % or higher. In addition, the content may be 5 wt % or lower, 4.5 wt % or lower, 4 wt % or lower, 3.5 wt % or lower, 3 wt % or lower, 2.5 wt % or lower, 2 wt % or lower, 1.5 wt % or lower, 1.2 wt % or lower, 1 wt % or lower, 0.8 wt % or lower, 0.6 wt % or lower, 0.4 wt % or lower, or 0.2 wt % or lower.

In another exemplary embodiment, the content of the glycerin may be 5-20 wt % based on the total weight of the skin cosmetic solution. If the content exceeds 20 wt %, usability may be poor due to increased viscosity, difficulty of filtration, etc. If the content is below 5 wt %, the effect of extraction may decrease remarkably. In an aspect, the content may be 5 wt % or higher, 7 wt % or higher, 9 wt % or higher, 11 wt % or higher, 13 wt % or higher, 15 wt % or higher, 17 wt % or higher, or 19 wt % or higher. In addition, the content may be 20 wt % or lower, 18 wt % or lower, 16 wt % or lower, 14 wt % or lower, 12 wt % or lower, 10 wt % or lower, 8 wt % or lower, or 6 wt % or lower.

In another exemplary embodiment, the content of the glycerin derivative may be 0.01-10 wt % based on the total weight of the skin cosmetic solution. If the content exceeds 10 wt %, usability may be poor due to increased viscosity, difficulty of filtration, etc. If the content is below 0.01 wt %, the effect of extraction may decrease remarkably. In an aspect, the content may be 0.01 wt % or higher, 0.05 wt % or higher, 0.08 wt % or higher, 0.1 wt % or higher, 0.12 wt % or higher, 0.14 wt % or higher, 0.2 wt % or higher, 0.4 wt % or higher, 0.6 wt % or higher, 0.8 wt % or higher, 1 wt % or higher, 4 wt % or higher, 6 wt % or higher, or 8 wt % or higher. In addition, the content may be 8 wt % or lower, 6 wt % or lower, 4 wt % or lower, 1 wt % or lower, 0.8 wt % or lower, 0.6 wt % or lower, 0.4 wt % or lower, 0.2 wt % or lower, 0.14 wt % or lower, 0.12 wt % or lower, 0.1 wt % or lower, 0.08 wt % or lower, 0.05 wt % or lower, or 0.02 wt % or lower.

According to an aspect of the present disclosure, a weight ratio of glycerin:butylene glycol may be 1:0.5-5 or higher. In an aspect, the ratio may be 1:0.5 or higher, 1:0.7 or higher, 1:0.9 or higher, 1:1.0 or higher, 1:1.2 or higher, 1:1.4 or higher, 1:1.6 or higher, 1:1.8 or higher, 1:2 or higher, 1:2.5 or higher, 1:2.8 or higher, 1:3 or higher, 1:3.5 or higher, 1:4 or higher, or 1:4.5 or higher. In addition, the ratio may be 1:5 or lower, 1:4.5 or lower, 1:4 or lower, 1:3.5 or lower, 1:3 or lower, 1:2.5 or lower, 1:2 or lower, 1:1.5 or lower, 1:1.2 or lower, 1:1 or lower, 1:0.8 or lower, or 1:0.6 or lower.

In an exemplary embodiment, a weight ratio of butylene glycol:propanediol may be 1:0.04-2. In an aspect, the ratio may be 1:0.04 or higher, 1:0.06 or higher, 1:0.08 or higher, 1:0.1 or higher, 1:0.2 or higher, 1:0.4 or higher, 1:0.6 or higher, 1:0.8 or higher, 1:1 or higher, 1:1.2 or higher, 1:1.4 or higher, 1:1.6 or higher, or 1:1.8 or higher. In addition, the ratio may be 1:2 or lower, 1:1.8 or lower, 1:1.6 or lower, 1:1.4 or lower, 1:1.2 or lower, 1:1 or lower, 1:0.8 or lower, 1:0.6 or lower, 1:0.4 or lower, 1:0.2 or lower, 1:0.1 or lower, 1:0.08 or lower, or 1:0.06 or lower.

In another exemplary embodiment, a weight ratio of propanediol:hexanediol may be 1:0.005-5. In an aspect, the ratio may be 1:0.005 or higher, 1:0.01 or higher, 1:0.05 or higher, 1:0.1 or higher, 1:0.5 or higher, 1:1 or higher, 1:2 or higher, 1:3 or higher, or 1:4 or higher. In addition, the ratio may be 1:5 or lower, 1:4 or lower, 1:3 or lower, 1:2 or lower, 1:1 or lower, 1:0.5 or lower, 1:0.1 or lower, 1:0.05 or lower, 1:0.01 or lower, or 1:0.008 or lower.

In another exemplary embodiment a weight ratio of hexanediol:glycerin derivative may be 1:0.002-100. In an aspect, the ratio may be 1:0.002 or higher, 1:0.005 or higher, 1:0.01 or higher, 1:0.05 or higher, 1:0.1 or higher, 1:0.5 or higher, 1:1 or higher, 1:5 or higher, 1:10 or higher, 1:20 or higher, 1:30 or higher, 1:40 or higher, 1:50 or higher, or 1:80 or higher. In addition, the ratio may be 1:100 or lower, 1:80 or lower, 1:60 or lower, 1:40 or lower, 1:30 or lower, 1:20 or lower, 1:10 or lower, 1:5 or lower, 1:1 or lower, 1:0.5 or lower, 1:0.1 or lower, 1:0.05 or lower, 1:0.01 or lower, or 1:0.005 or lower.

In another exemplary embodiment, the content of the D-glucose may be 0.1-10 wt % based on the total weight of the skin cosmetic solution. If the content exceeds 10 wt %, usability may be poor due to increased viscosity, difficulty of filtration, etc. If the content is below 0.1 wt %, the effect of extraction may decrease remarkably. In an aspect the content of the D-glucose may be 0.1 wt % or higher, 0.5 wt % or higher, 1 wt % or higher, 1.5 wt % or higher, 2 wt % or higher, 2.5 wt % or higher, 3 wt % or higher, 3.5 wt % or higher, 4 wt % or higher, 4.5 wt % or higher, 5 wt % or higher, 5.5 wt % or higher, 6 wt % or higher, 7 wt % or higher, 8 wt % or higher, or 9 wt % or higher. In addition, the content may be 10 wt % or lower, 9 wt % or lower, 8 wt % or lower, 7 wt % or lower, 6 wt % or lower, 5.5 wt % or lower, 5 wt % or lower, 4.5 wt % or lower, 4 wt % or lower, 3.5 wt % or lower, 3 wt % or lower, 2.5 wt % or lower, 2 wt % or lower, 1.5 wt % or lower, 1 wt % or lower, or 0.5 wt % or lower.

In another exemplary embodiment, the content of the betaine may be 0.1-10 wt % based on the total weight of the skin cosmetic solution. If the content exceeds 10 wt %, usability may be poor due to increased viscosity, difficulty of filtration, etc. If the content is below 0.1 wt %, the effect of extraction may decrease remarkably. In an aspect, the content of the betaine may be 0.1 wt % or higher, 0.5 wt % or higher, 1 wt % or higher, 1.5 wt % or higher, 2 wt % or higher, 2.5 wt % or higher, 3 wt % or higher, 3.5 wt % or higher, 4 wt % or higher, 4.5 wt % or higher, 5 wt % or higher, 5.5 wt % or higher, 6 wt % or higher, 7 wt % or higher, 8 wt % or higher, or 9 wt % or higher. In addition, the content may be 10 wt % or lower, 9 wt % or lower, 8 wt % or lower, 7 wt % or lower, 6 wt % or lower, 5.5 wt % or lower, 5 wt % or lower, 4.5 wt % or lower, 4 wt % or lower, 3.5 wt % or lower, 3 wt % or lower, 2.5 wt % or lower, 2 wt % or lower, 1.5 wt % or lower, 1 wt % or lower, or 0.5 wt % or lower.

In an exemplary embodiment, the *Artemisia* extract may be one extracted by ultrasonic extraction, room-temperature extraction, cold brewing extraction or reflux condensation extraction, although not being limited thereto.

In another exemplary embodiment, the *Artemisia* extract may be one extracted at 85-95° C. For example, the *Artemisia* extract may be one extracted at 85° C. or higher, 86° C. or higher, 87° C. or higher, 88° C. or higher, 89° C. or higher, 90° C. or higher, 91° C. or higher, 92° C. or higher, 93° C. or higher, or 94° C. or higher. In addition, it may be one extracted at 95° C. or lower, 94° C. or lower, 93° C. or lower, 92° C. or lower, 91° C. or lower, 90° C. or lower, 89° C. or lower, 88° C. or lower, 87° C. or lower, or 86° C. or lower.

In another exemplary embodiment, the *Artemisia* extract may be one extracted for 20-30 hours. For example, the *Artemisia* extract may be one extracted for 20 hours or longer, 22 hours or longer, 24 hours or longer, 26 hours or longer, or 28 hours or longer. In addition, it may be one extracted for 30 hours or shorter, 28 hours or shorter, 26 hours or shorter, 24 hours or shorter, or 22 hours or shorter.

In an exemplary embodiment, the *Artemisia* extract may be contained in an amount of 0.001-100 wt % based on the total weight of the composition in order to achieve the desired effect. In another exemplary embodiment, the content of the *Artemisia* extract may be 0.001 wt % or higher, 0.01 wt % or higher, 0.1 wt % or higher, 1 wt % or higher, 10 wt % or higher, 20 wt % or higher, 30 wt % or higher, 40 wt % or higher, 50 wt % or higher, 60 wt % or higher, 70 wt % or higher, 80 wt % or higher, or 90 wt % or higher, and 100 wt % or lower, 90 wt % or lower, 80 wt % or lower, 70 wt % or lower, 60 wt % or lower, 50 wt % or lower, 40 wt % or lower, 30 wt % or lower, 20 wt % or lower, 10 wt % or lower, 1 wt % or lower, or 0.1 wt % or lower, based on the total weight of the composition.

In an exemplary embodiment, the composition may be a cosmetic composition.

The cosmetic composition according to an aspect of the present disclosure may contain a cosmetically or dermatologically acceptable medium or base. It may be prepared into any formulation suitable for topical application. For example, it may be provided in the form of a solution, a gel, a solid, an anhydrous paste, an oil-in-water emulsion, a suspension, a microemulsion, a microcapsule, a microgranule, an ionic (liposome) or non-ionic vesicular dispersion, a cream, a lotion, a powder, an ointment, a spray or a concealer stick. These formulations may be prepared according to common methods in the art. The cosmetic composition may also be used as an aerosol composition further containing a propellant compressed into a foam.

The cosmetic composition is not particularly limited in formulation, which may be selected adequately depending on purposes. For example, it may be prepared into a skin lotion, a skin softener, a skin toner, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a cleansing water, a powder, a body lotion, a body cream, a body oil, a body cleanser, a body essence, etc.

When the formulation of the present disclosure is a paste, a cream or a gel, an animal fiber, a plant fiber, a wax, paraffin, starch, tragacanth, a cellulose derivative, polyethylene glycol, silicone, bentonite, silica, talc, zinc oxide, etc. may be used as a carrier ingredient.

When the formulation of the present disclosure is a powder or a spray, lactose, talc, silica, aluminum hydroxide, calcium silicate or polyamide powder may be used as a carrier ingredient. In particular, a spray may further contain a propellant such as chlorofluorohydrocarbon, propane/butane or dimethyl ether.

When the formulation of the present disclosure is a solution or an emulsion, a solvent, a solubilizer or an emulsifier may be used as a carrier ingredient. Examples include water, ethanol, isopropanol, ethyl carbonate, ethyl acetate, benzyl alcohol, benzyl benzoate, propylene glycol, 1,3-butylene glycol, a glycerol aliphatic ester, polyethylene glycol or a fatty acid ester of sorbitan.

When the formulation of the present disclosure is a suspension, a liquid diluent such as water, ethanol or propylene glycol, suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

When the formulation of the present disclosure is a surfactant-containing cleanser, an aliphatic alcohol sulfate, an aliphatic alcohol ether sulfate, sulfosuccinic acid monoester, isethionate, an imidazolinium derivative, methyl taurate, sarcosinate, a fatty acid amide ether sulfate, an alkyl amidobetaine, aliphatic alcohol, a fatty acid glyceride, a fatty acid diethanolamide, a vegetable oil, a lanolin derivative, an ethoxylated glycerol fatty acid ester, etc. may be used as a carrier ingredient.

In addition to the *Artemisia* extract, the cosmetic composition may further contain a functional additive and common ingredients contained in cosmetic compositions. The functional additive may be one or more ingredient selected from a group consisting of a water-soluble vitamin, an oil-soluble vitamin, a polypeptide, a polysaccharide, a sphingolipid and a seaweed extract.

In addition to the functional additive, the composition may further contain common ingredients contained in cosmetic compositions. The additional ingredients may be an oil, a fat, a humectant, an emollient, a surfactant, an organic or inorganic pigment, an inorganic powder, a UV absorbent, an antiseptic, a sterilizer, an antioxidant, a plant extract, a pH control agent, an alcohol, a colorant, a flavor, a blood circulation promoter, a cooling agent, an antiperspirant, purified water, etc.

Hereinafter, the present disclosure will be described in detail through examples and test examples. However, the following examples and test examples are for illustrative purposes only and it will be apparent to those of ordinary skill in the art that the scope of the present disclosure is not limited by the examples and test examples.

[Examples and Comparative Examples] Preparation of *Artemisia* Extract

*Artemisia* extracts were prepared by performing extraction with extraction solvents of Examples 1-2 and Comparative Examples 1-5 as described in Table 1.

Specifically, 1 g of the upper leaf of *Artemisia argyi* acquired from a farmhouse in Ganghwa Island was immersed in 1 kg of the extraction solvent of Examples 1-2 and Comparative Examples 1-5, extracted under reflux at 90° C. for 24 hours, and then filtered through a 0.45-μm filter.

TABLE 1

|  | Ex. 1 | Ex. 2 | Comp. Ex. 1 | Comp. Ex. 2 | Comp. Ex. 3 | Comp. Ex. 4 | Comp. Ex. 5 |
| --- | --- | --- | --- | --- | --- | --- | --- |
| Purified water | To 100 | To 100 | 100 | — | — | — | — |
| Ethanol | — | — | — | 100 | — | — | — |
| Ethyl acetate | — | — | — | — | 100 | — | — |
| Hexane | — | — | — | — | — | 100 | — |
| Isopropyl alcohol | — | — | — | — | — | — | 100 |
| Glycerin | 15 | 10 | — | — | — | — | — |
| 1,3-Butylene glycol | 20 | 10 | — | — | — | — | — |
| 1,3-Propanediol | 10 | — | — | — | — | — | — |
| 1,2-Hexanediol | 1 | 1 | — | — | — | — | — |
| Ethylhexylglycerin | 0.1 | 0.1 | — | — | — | — | — |
| D-Glucose | — | 5 | — | — | — | — | — |
| Betaine | — | 5 | — | — | — | — | — |

[Test Example 1] Evaluation of Skin Safety and Extraction Efficiency

The skin safety and extraction efficiency of the *Artemisia* extracts extracted with the extraction solvents of Examples 1-2 and Comparative Example 1-5 were evaluated.

Specifically, the skin safety was evaluated by a closed patch test (on the back) for 32 healthy female adults with an average age of 36 years (Those with psoriasis, acne, eczema or other skin diseases, pregnant women, lactating women and those who were taking contraceptives, antihistamines, etc. were excluded). After applying each sample (*Artemisia* extract) with an amount of 204 per chamber (IQ chamber), the patch was removed 24 hours later. Skin response was evaluated according to the CTFA guideline and the criteria of Frosch & Kligman.

And, the extraction efficiency was evaluated using a dried residue. Specifically, after drying 1 g of each sample at 105° C. for 4 hours, the quantity of the residue was compared. A larger quantity of the residue is translated into higher extraction efficiency (+++++:highest extraction efficiency/+:lowest extraction efficiency).

The result is given in Table 2.

TABLE 2

|  | Ex. 1 | Ex. 2 | Comp. Ex. 1 | Comp. Ex. 2 | Comp. Ex. 3 | Comp. Ex. 4 | Comp. Ex. 5 |
| --- | --- | --- | --- | --- | --- | --- | --- |
| Skin safety | ◯ | ◯ | ◯ | X | X | X | X |
| Extraction efficiency | +++ | +++ | + | ++++ | ++++ | ++++ | ++++ |

From Table 2, it can be seen that superior skin safety and extraction efficiency were achieved when the extraction solvents of Examples 1 and 2, which are the skin cosmetic solution according to the present disclosure, were used. In contrast, when organic solvents commonly used in general extraction methods such as ethanol, ethyl acetate, hexane or isopropyl alcohol were used (Comparative Examples 2-5), extraction efficiency was higher but the skin safety requirement was not satisfied. And, when purified water (Comparative Example 1) was used as the extraction solvent, the extraction efficiency was decreased significantly although there was no skin safety problem.

That is to say, it can be seen that Examples 1 and 2 according to the present disclosure, wherein the substances that can be used as cosmetic ingredients were mixed, can be used as skin cosmetic solutions (cosmetics) without solvent removal or additional processes because they can be applied safely to the skin without irritation unlike the organic solvents such as ethanol, ethyl acetate, hexane, isopropyl alcohol, etc. Accordingly, Examples 1 and 2 exhibit remarkably superior usability as compared to Comparative Examples since they can be applied directly to the skin as cosmetic compositions without additional processing of the extracted *Artemisia* extract. In addition, Examples 1 and 2 provide remarkably superior preservation of the extracted ingredients as compared to the existing solvents since they can effectively extract the useful ingredients of *Artemisia* as extraction solvents with minimized processing.

[Test Example 2] Evaluation of Skin Moisturizing Effect of *Artemisia* Extract

The skin moisturizing effect of the *Artemisia* extract extracted with the extraction solvent of Example 1 was evaluated.

The skin moisturizing effect was evaluated by measuring water content before and after (1 hour) applying the *Artemisia* extract on the forearm for 10 women aged 29-38 years (about 33.2 years on average). Specifically, the water content was measured before and after (1 hour) the application of the *Artemisia* extract using Corneometer® CM 825 (C+K, Germany). The measurement was made 3 times and then averaged. The result is shown in FIG. 1.

From FIG. 1, it can be seen that the water content in the skin is increased greatly when the *Artemisia* extract extracted with the extraction solvent of Example 1 according to the present disclosure was used.

[Test Example 3] Evaluation of Skin Anti-Inflammation Effect of *Artemisia* Extract The skin anti-inflammation effect of the *Artemisia* extract extracted with the extraction solvent of Example 1 was evaluated.

The skin anti-inflammation effect was evaluated by analyzing the expression of COX-2 (cytochrome c oxidase subunit 2) RNA by quantitative PCR. Specifically, $2 \times 10^5$ human neonatal epidermal keratinocytes (HEKn; Lonza) were seeded onto a 6-well plate and cultured in a KBM-Gold medium (Lonza) under the condition of 37° C. and 5% $CO_2$ for 24 hours. After treating each well with 20 ng/mL IFNγ for 24 hours and then treating with the *Artemisia* extract extracted with the extraction solvent of Example 1 at different concentrations, the cells were lysed 24 hours later using a Trizol reagent (Invitrogen Carlsbad, Calif., USA) and RNA was extracted from the cells. After quantifying the isolated RNA, cDNA was synthesized using a Superscript reverse transcriptase (RT) II kit (Invitrogen) and real-time polymerase chain reaction (RT-PCR) was conducted using a Taqman gene expression assay kit. The RPLPO gene was used as an internal control gene, and the relative expression level of COX2 was quantitated using the Ct value. The result is shown in FIG. 2.

Figure 2:
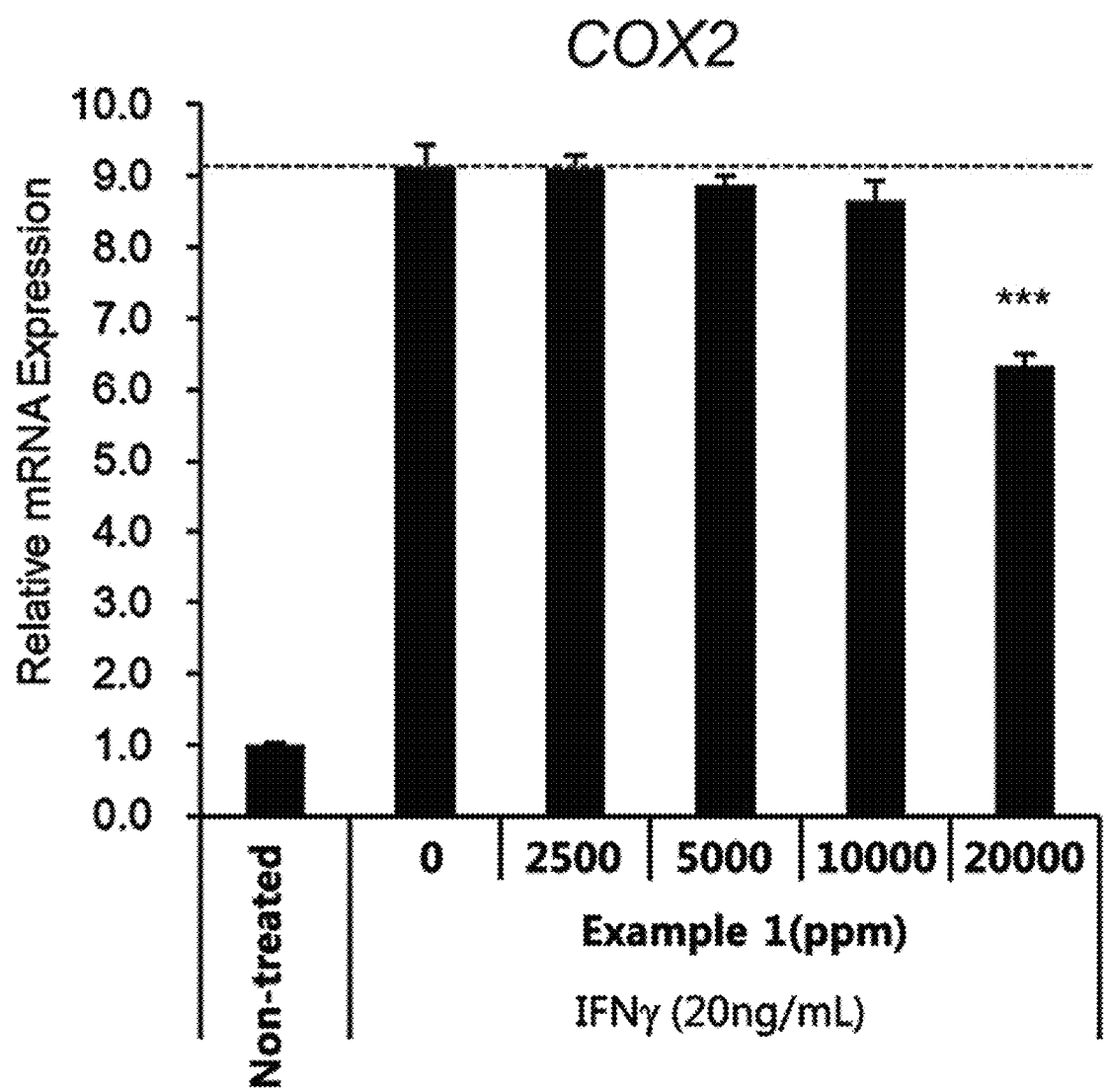
FIG. 2 shows a result of evaluating the skin anti-inflammation effect of an *Artemisia* extract according to the present disclosure in Test Example 3.

From FIG. 2, it can be seen that the expression level of COX2, which was significantly increased by the treatment with IFNγ, was decreased in a concentration-dependent manner due to the treatment with the *Artemisia* extract of Example 1 according to the present disclosure. In particular, it can be seen that the expression level of COX2 is decreased greatly when the *Artemisia* extract of Example 1 was treated at a concentration of 20000 ppm.

[Formulation Example 1] Nourishing Lotion

A nourishing lotion was prepared by extracting 1 wt % of *Artemisia* as described in Example 1 according to an aspect of the present disclosure and then adding 5 wt % (based on the total weight of the extract) of squalane to the extract.

[Formulation Example 2] Softening Lotion

A softening lotion was prepared by extracting 5 wt % of *Artemisia* as described in Example 1 according to an aspect of the present disclosure and then adding 0.5 wt % (based on the total weight of the extract) of liquid paraffin, 5 wt % of caprylic/capric triglyceride, 1.5 wt % of polysorbate 60, 5 wt % of squalane and 4 wt % of beeswax to the extract.

[Formulation Example 3] Pack

A pack was prepared by extracting 3 wt % of *Artemisia* as described in Example 1 according to an aspect of the present disclosure, adding 0.3 wt % (based on the total weight of the extract) of PEG 12 nonyl phenyl ether, 0.1 wt % of allantoin and 13 wt % of polyvinyl alcohol to the extract and then applying the mixture onto surface of a pack.

What is claimed is:
1. A method for skin anti-inflammation, which comprises preparing an *Artemisia* extract using a skin cosmetic solution as an extraction solvent; and administering the *Artemisia* extract to a subject in need thereof,
wherein the skin cosmetic solution comprises
one or more selected from the group consisting of butylene glycol, propanediol, and hexanediol;
one or more of glycerin and a glycerin derivative; and
one or more of D-glucose and betaine,
wherein a content of the D-glucose is 0.1-10 wt % based on a total weight of the skin cosmetic solution; or a content of the betaine is 0.1-10 wt % based on the total weight of the skin cosmetic solution, and
wherein the *Artemisia* extract is administered in a form of a cosmetic composition and the *Artemisia* extract is comprised in an amount of 100 wt % based on total weight of the cosmetic composition.
2. The method according to claim 1, wherein the butylene glycol is 1,3-butylene glycol, the propanediol is 1,3-propanediol, and the hexanediol is 1,2-hexanediol.
3. The method according to claim 1, wherein the glycerin derivative is ethylhexylglycerin.
4. The method according to claim 1, wherein
a content of the butylene glycol is 10-25 wt % based on the total weight of the skin cosmetic solution;
a content of the propanediol is 1-20 wt % based on the total weight of the skin cosmetic solution; or
a content of the hexanediol is 0.1-5 wt % based on the total weight of the skin cosmetic solution.
5. The method according to claim 1, wherein a content of the glycerin is 5-20 wt % based on the total weight of the skin cosmetic solution; or a content of the glycerin derivative is 0.01-10 wt % based on the total weight of the skin cosmetic solution.

\* \* \* \* \*